(12) United States Patent
Goswami et al.

(10) Patent No.: US 10,864,294 B1
(45) Date of Patent: *Dec. 15, 2020

(54) ENHANCEMENT OF PHOTOCATALYTIC EFFECT WITH SURFACE ROUGHNESS IN PHOTOCATALYTIC REACTORS

(71) Applicants: Dharendra Yogi Goswami, Tampa, FL (US); Elias K. Stefanakos, Tampa, FL (US); Yangyang Zhang, Tampa, FL (US)

(72) Inventors: Dharendra Yogi Goswami, Tampa, FL (US); Elias K. Stefanakos, Tampa, FL (US); Yangyang Zhang, Tampa, FL (US)

(73) Assignee: University of South Florida, Tampa, FL (US)

( * ) Notice: Subject to any disclaimer, the term of this patent is extended or adjusted under 35 U.S.C. 154(b) by 58 days.

This patent is subject to a terminal disclaimer.

(21) Appl. No.: 15/683,312

(22) Filed: Aug. 22, 2017

Related U.S. Application Data

(63) Continuation of application No. 14/511,970, filed on Oct. 10, 2014, now Pat. No. 9,889,221.

(60) Provisional application No. 61/889,329, filed on Oct. 10, 2013.

(51) Int. Cl.
*A61L 9/20* (2006.01)

(52) U.S. Cl.
CPC .................................. *A61L 9/205* (2013.01)

(58) Field of Classification Search
CPC ....................................................... A61L 9/205

USPC ......................................................... 422/122
See application file for complete search history.

(56) References Cited

U.S. PATENT DOCUMENTS

| | | | |
|---|---|---|---|
| 5,933,702 A | 8/1999 | Goswami | |
| 6,217,999 B1 | 4/2001 | Zhang et al. | |
| 7,691,342 B2 | 4/2010 | Sahle-Demessie et al. | |
| 7,858,552 B2 | 12/2010 | Boyd et al. | |
| 2010/0209312 A1* | 8/2010 | Pastor | A61L 9/205 422/186.3 |
| 2013/0315786 A1* | 11/2013 | Horie | B01J 21/063 422/120 |
| 2015/0250914 A1* | 9/2015 | Aeifin | A61L 9/205 422/4 |

OTHER PUBLICATIONS

Antonia RA, Luxton RE. Response of a turbulent boundary layer to an upstanding step change in surface roughness. J Basic Eng 1971;93:22-33.

(Continued)

*Primary Examiner* — Holly Kipouros
(74) *Attorney, Agent, or Firm* — Nicholas Pfeifer; Smith & Hopen, P.A.

(57) ABSTRACT

Photocatalysis is a promising technique for remediation of indoor air pollution. The present invention focuses on the enhancement of the effectiveness of the photocatalytic process by the introduction of artificial roughness on the interior reactor surface. Artificial roughness elements on the catalytic surface enhance the turbulence intensity close to the catalytic surface. The enhanced turbulence intensity translates to an increase in the mass transfer of airborne contaminants to the catalyst surface, improving the efficiency of photocatalysis.

12 Claims, 15 Drawing Sheets
(7 of 15 Drawing Sheet(s) Filed in Color)

(56) References Cited

OTHER PUBLICATIONS

Austin BS, Greenfield SM, Weir BR, Anderson GE, Behar JV. Modeling the indoor environment. Environ Sci Technol 1992;26:851-8.

Begum BA, Paul SK, Hossain MD, Biswas SK, Hopke PK. Indoor air pollution from particulate matter emissions in different households in rural areas of Bangladesh. Building Environ 2009;44, pp. 898-903.

Birnie M, Gillott M, Riffat S. Incorporating mass transfer theory to model continuous flow type photocatalytic reactors for integration into novel low energy ventilation systems. J Energy Inst 2006;79, 3, pp. 131-138.

Chen F, Yang X, Mak HKC, Chan DWT. Photocatalytic oxidation for antimicrobial control in built environment: a brief literature overview. Building Environ 2010;45, pp. 1747-1754.

Chen Q, Meng J-A. Field synergy analysis and optimization of the convective mass transfer in photocatalytic oxidation reactors. Int J Heat Mass Transfer 2008;51, pp. 2863-2870.

Cui J, Patel VC, Lin CL. Large-eddy simulation of turbulent flow in a channel with rib roughness. Int J Heat Fluid Flow 2003;24:372-88.

Daisey JM, Angell WJ, Apte MG. Indoor air quality, ventilation and health symptoms in schools: an analysis of existing information. Indoor Air 2003;13, pp. 53-64.

Dibble LA, Raupp GB. Fluidized-bed photocatalytic oxidation of trichloroethylene in contaminated airstreams. Environ Sci Technol 1992;26:492-5.

Feigley CE, Do TH, Khan J, Lee E, Schnaufer ND, Salzberg DC. Deriving realistic source boundary conditions for a CFD simulation of concentrations in workroom air. Ann Occup Hyg 2011;55:410-20.

Goswami DY. Decontamination of ventilation systems using photocatalytic air cleaning technology. J Sol Energy Eng—Trans ASME 2003;125:359-65.

Gupta S, Khare M, Goyal R. Sick building syndrome—a case study in a multistory centrally air-conditioned building in the Delhi City. Building Environ 2007;42, pp. 2797-2809.

Hanjalic K, Launder BE. Fully developed asymmetric flow in a plane channel. J Fluid Mechanics 1972;51:301-35.

Hossain MM, Raupp GB, Hay SO, Obee TN. Three-dimensional developing flow model for photocatalytic monolith reactors. AIChE J 1999;45:1309-21.

Huang Y, Zheng H, Mao WW, Li GH, Ye B. Numerical simulation of air-soil two-phase flow based on turbulence modeling. Nat Hazards 2011;58:311-23.

Husken et al., Experimental study of photocatalytic concrete products for air purification, Building and Environment, 2009, 44, pp. 2463-2474.

Jones AP. Indoor air quality and health. Atmos Environ 1999;33:4535-64.

Kataoka K, Kamiyama Y, Hashimoto S, Komai T. Mass-transfer between a plane surface and an impinging turbulent jet—the influence of surface—pressure fluctuations. J Fluid Mechanics 1982;119:91-105.

Kolarik J, Toftum J. The impact of a photocatalytic paint on indoor air pollutants: sensory assessments. Building Environ 2012;57, pp. 396-402.

Kumar S, Saini RP. CFD based performance analysis of a solar air heater duct provided with artificial roughness. Renew Energy 2009;34:1285-91.

Larson SA, Widegren JA, Falconer JL. Transient studies of 2-propanol photocatalytic oxidation on titania. J Catal 1995;157:611-25.

Lee SC, Guo H, Li WM, Chan LY. Inter-comparison of air pollutant concentrations in different indoor environments in Hong Kong. Atmos Environ 2002;36, pp. 1929-1940.

Mo J, Zhang Y, Yang R. Novel insight into VOC removal performance of photocatalytic oxidation reactors. Indoor Air 2005;15:291-300.

Momin AME, Saini JS, Solanki SC. Heat transfer and friction in solar air heater duct with V-shaped rib roughness on absorber plate. Int J Heat Mass Transfer 2002;45:3383-96.

Moraveji MK, Sajjadi B, Jafarkhani M, Davarnejad R. Experimental investigation and CFD simulation of turbulence effect on hydrodynamic and mass transfer in a packed bed airlift internal loop reactor. Int Commun Heat Mass Transfer 2011;38:518-24.

Obee TN, Brown RT. TiO2 photocatalysis for indoor air applications—effects of humidity and trace contaminant levels on the oxidation rates of formaldehyde, toluene, and 1,3-butadiene. Environ Sci Technol 1995;29:1223-31.

Ong MC, Utnes T, Holmedal LE, Myrhaug D, Pettersen B. Numerical simulation of flow around a circular cylinder close to a flat seabed at high Reynolds numbers using a k-epsilon model. Coastal Eng 2010;57:931-47.

Passalia C, Martinez Retamar ME, Alfano OM, Brandi RJ. Photocatalytic degradation of formaldehyde in gas phase on TiO2 films: a kinetic study. Int J Chem Reactor Eng 2010;8, pp. 1-30.

Perry AE, Schofiel Wh, Joubert PN. Rough wall turbulent boundary layers. J Fluid Mechanics 1969;37:383-413.

Queffeulou A, Geron L, Archambeau C, Le Gall H, Marquaire PM, Zahraa O. Kinetic study of acetaldehyde photocatalytic oxidation with a thin film of TiO2 coated on stainless steel and CFD modeling approach. Ind Eng Chem Res 2010; 49:6890-7.

Ray, Design, modelling and experimentation of a new large-scale photocatalytic reactor for water treatment, Chemical Engineering Science 54 (1999) pp. 3113-3125.

Riffat SB, Zhao X Preliminary study of the performance and operating characteristics of a mop-fan air cleaning system for buildings. Building Environ 2007;42:3241-52.

Salvado-Estivill I, Hargreaves DM, Puma GL. Evaluation of the intrinsic photocatalytic oxidation kinetics of indoor air pollutants. Environ Sci Technol 2007;41:2028-35.

Sanitjai S, Goldstein RJ. Effect of free stream turbulence on local mass transfer from a circular cylinder. Int J Heat Mass Transfer 2001;44, pp. 2863-2875.

Sun R-B, Xi Z-G, Chao F-H, Zhang W, Zhang H-S, Yang D-F. Decomposition of low-concentration gas-phase toluene using plasma-driven photocatalyst reactor. Atmos Environ 2007;41:6853-9.

Vohra A, Goswami DY, Deshpande DA, Block SS. Enhanced photocatalytic disinfection of indoor air. Appl Catal B 2006;64:57-65.

Wang L, Hejcik J, Sunden B. PIV measurement of separated flow in a square channel with streamwise periodic ribs on one wall. J Fluids Eng—Trans ASME 2007;129:834-41.

Yang R, Zhang Y, Xu Q, Mo J. A mass transfer based method for measuring the reaction coefficients of a photocatalyst. Atmos Environ 2007;41:1221-9.

Zhang Y, Ram MK, Stefanakos EK, Goswami DY. Synthesis, characterization, and applications of ZnO nanowires. J Nanomaterials 2012, pp. 1-22.

Zhang et al., Effect of photocatalytic surface roughness on reactors effectiveness for indoor air cleaning, Building and Environment, 2013, 61, pp. 188-196.

Goswami DY, Trivedi DM, Block SS. Photocatalytic disinfection of indoor air. J Sol Energy Eng—Trans ASME 1997;119:92-6.

Kestin J, Wood RT. Influence of turbulence on mass transfer from cylinders. J Heat Transfer 1971;93:321-7.

Prasad BN, Saini JS. Optimal thermohydraulic performance of artificially roughened solar air heaters. Sol Energy 1991;47:91-6.

Simonich JC, Bradshaw P. Effect of free-stream turbulence on heat-transfer through a turbulent boundary-layer. J Heat Transfer—Trans ASME 1978;100:671-7.

Vohra A. Photocatalytic disinfection of indoor air: effect of relative humidity and surface roughness of photocatalytic reactor. University of Florida; 2005, pp. 1-165.

Varun et al., A review on roughness geometry used in solar air heaters, Solar Energy 81 (2007) pp. 1340-1350.

Chaube et al., Effect of roughness shape on heat transfer and flow friction characteristics of solar air heater with roughened absorber plate, Advanced Computational Methods in Heat Transfer IX, WIT Transactions on Engineering Sciences, 2006, vol. 53, pp. 43-51.

(56) References Cited

OTHER PUBLICATIONS

Karwa et al., Heat transfer coefficient and friction factor correlations for the transitional flow regime in rib-roughened rectangular ducts, International Journal of Heat and Mass Transfer, vol. 42 (1999) pp. 1597-1615.

* cited by examiner

ENHANCEMENT OF PHOTOCATALYTIC EFFECT WITH SURFACE ROUGHNESS IN PHOTOCATALYTIC REACTORS

CROSS-REFERENCE TO RELATED APPLICATIONS

This nonprovisional application is a continuation of and claims priority to nonprovisional application Ser. No. 14/511,970, entitled "ENHANCEMENT OF PHOTOCATALYTIC EFFECT WITH SURFACE ROUGHNESS IN PHOTOCATALYTIC REACTORS," filed Oct. 10, 2014 by the same inventors, which claims priority to provisional application No. 61/889,329, entitled "ENHANCEMENT OF PHOTOCATALYTIC EFFECT WITH SURFACE ROUGHNESS IN PHOTOCATALYTIC REACTORS," filed Oct. 10, 2013 by the same inventors.

BACKGROUND OF THE INVENTION

1. Field of the Invention

This invention relates, generally, to remediation of air pollution. More specifically, it relates to a photocatalytic remediation of indoor air pollution.

2. Brief Description of the Prior Art

Indoor air quality has become a great concern due to the increased time spent indoors. Most people spend more than 90% of their time in indoor environments such as a home, office, car, shopping center, etc. [1, 2]. Studies show that the level of pollutants indoors is much higher than that of outdoor environments [3, 4]. Photocatalysis is becoming an extremely important method of disinfecting and cleaning indoor air. Photocatalysis is a promising technique for the remediation of air pollution because it is able to oxidize low concentrations of organic contaminants into benign products [5]. Photocatalysis utilizes semiconductors like $TiO_2$, ZnO, $WO_3$ or $Fe_2O_3$ to carry out a photo-induced oxidation process to breakdown volatile organic compounds (VOCs) and inactivate bacteria and viruses [6].

In order for photocatalysis to be effective, it is necessary for the contaminants to come in close contact with the photocatalyst on which a light of appropriate wavelength is incident. In other words, the effectiveness of this process is dependent on the probability of the contaminant particles being close to the catalytic surface. As the air flows past a catalytic surface, a boundary layer forms along the surface, which does not allow mixing of the air resulting in extremely low probability of contaminant particles coming in contact with the catalytic surface.

There are various photocatalytic reactors that have already been reported in the prior art, such as plate reactors and honeycomb reactors [7-16]. Most of the air reactors utilize a surface-coated catalyst configuration with the airflow being parallel to the catalyst surface. When the air flows parallel to a smooth catalytic surface, a laminar sublayer is formed over the surface that impedes the mass transfer of reactants to the catalyst and the reaction products to the main flow, thus adversely affecting the photocatalytic reaction rate. Moreover, indoor air pollutant levels are typically on the order of parts per million (ppm) [17, 18], which requires more mass transfer for effective heterogeneous photocatalysis. Although mass transfer plays a significant role in photocatalysis, it has not received much attention in the photocatalytic field. There are only a few research groups that have considered the effect of mass transfer in their photocatalytic study.

Mo et al. [19] developed a mass transfer units (NTUm) method in which they considered three key factors, including reactor area (A*), mass transfer (Stm), and reaction effectiveness (h), to study the performance of a photocatalytic reactor for removing VOCs. Passalia et al. [20] studied the photocatalytic degradation of formaldehyde and presented a non-linear expression based on mass balance and rate expression to estimate the kinetic parameters. Bimie et al. [21] investigated the influence of species mass transfer on the overall reaction rate of a flat plate photoreactor and developed a kinetic model incorporating the mass transfer theory.

Although some researchers have started to pay attention to the mass transfer in the kinetic models study, very few have studied how to increase the mass transfer in a photocatalytic reactor. The conventional method of increasing the mass transfer on the catalyst surface is by increasing the airflow rate in the reactor [22-24]. However, increasing the airflow rate reduces the residence time of the pollutants and leads to incomplete contaminant destruction and more intermediates. An ideal reactor design would be one that enhances the mass transfer rate of the contaminants to the catalyst surface and also increases the residence time.

Chen and Meng [25] developed a convective mass transfer field synergy equation with a specific boundary condition for photocatalytic oxidation reactors. By using the field synergy equation, the optimal velocity pattern in the reactor channel could be obtained. Based on the optimal flow pattern, they introduced discrete inclined ribs on the surface of the reactor channel to produce vortex flow pattern. Their experimental study showed that the contaminant removal effectiveness is increased compared to a smooth plate reactor. However, Chen and Meng failed to optimize the size, shape, or arrangement of the ribs to match the flow pattern in the reactor channel.

Vohra [26] described a commercially available reactor, in which the catalyst is coated on a non-uniform rough surface as the basis for his study of the effect of roughness on the turbulence of airflow on the surface. Vohra further stated that the catalytic coating on a rough surface was highly effective in the destruction of contaminants when compared to a similar reactor configuration without surface roughness elements. However, the study failed to determine the optimum surface roughness shape and geometry to maximize the effectiveness of photocatalytic air cleaning. Based on Vohra's study, it is assumed that roughness elements on the catalyst surface will increase the mass transport of the contaminants to the catalyst surface and thus lead to an increase in the effectiveness of photocatalysis.

The impact of surface roughness on the characteristics of fluid flow has been widely studied. It has been accepted that surface roughness elements have a great effect on the turbulent flow structure [27-30]. An early study, performed by Perry et al. [27], analyzed the effect of surface rib roughness on turbulent flow, comparing different pitch ratios of square roughness elements. The researchers proposed two primary types of square roughness elements that were classified as either d-type or k-type based on the pitch ratio (p/e), where 'p' is the pitch and 'e' is the height of roughness (See FIG. 1). The d-type roughness, in which the pitch ratio (p/e) is less than four, was characterized by a fully separated flow over the inter-rib vortex and thus did not affect the main flow. On the other hand, the k-type roughness, in which the pitch ratio (p/e) is greater than four, was characterized by a separated flow over the initial rib that became partially reattached before encountering the upstream face of the next rib and led to vortices and mixing eddies. More recently, emphasis has been given to numerical investigations of turbulent flow over rough surfaces to provide a better understanding of the turbulence characteristics. A computational study by Cui et al. [30] further explored the effect of rib spacing for turbulent channel flow exhibiting either d-type or k-type roughness. In d-type roughness, the separation eddies were confined to the gaps between the ribs. For k-type roughness, flow separation and reattachment occurs between two adjoining ribs. Subsequently, much larger and more frequent eddies are thrown into the outer flow, resulting in a strong interaction between the roughness layer and the outer flow. The experimental studies by Wang et al. [31] supported the results of Cui et al. [30].

A number of reports have shown that the roughness elements lead to an enhanced mass/heat transport [32-35]. The major effect of roughness elements is enhancing turbulent mixing [30]. An experimental study, conducted by Simonich and Bradshaw [34], reported a 5% increase in the heat transfer for every 1% increase in the turbulence intensity. Sanitjai and Goldstein [36] reported that the mass transfer (Sherwood number) increases about 60% as the free stream turbulence intensity increases by 23% in their experimental study of the effect of free stream turbulence on the local mass transfer from a circular cylinder. Moravejin et al. [37] also reported that mass transfer increased greatly with increased turbulence in their experimental investigation. Although the effect of surface roughness elements in enhancing heat/mass transfer is known, its effect on photocatalytic reactors has not been previously investigated.

Accordingly, what is needed is an improved photocatalytic reactor utilizing artificial roughness elements on the catalytic surface to enhance turbulence intensity, thus resulting in increased mass transfer and improved rate of photocatalysis. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an improved photocatalytic reactor utilizing artificial roughness elements on the catalytic surface to enhance turbulence intensity is now met by a new, useful, and nonobvious invention.

The novel structure includes an inlet section fluidly coupled to a reactor section that is fluidly coupled to an outlet section, wherein the reactor section includes a reactor catalyst surface exposed to a light source. The reactor catalyst surface contains a plurality of roughness elements to increase turbulence in the air flowing through the reactor section. Each roughness element further includes a pitch ratio of 10, a relative height ratio of 0.05, an element roughness width to channel height ratio of 0.01, and a relative width ratio of 0.02. Additionally, each roughness element extends, preferably, the width of the reactor catalyst surface. In a certain embodiment, each roughness element has a cross-section shaped like an isosceles triangle, where the isosceles triangle shape has a bottom angle between 75 and 89 degrees and a zenith angle of 30 degrees. Moreover, the reactor catalyst surface is preferably coated with a photocatalyst coating to improve the efficiency of the reactor.

In a certain embodiment, the present invention includes a fluid source moving fluid through the inlet section into the reactor section and out of reactor section through the outlet section. The fluid preferably moves through the reactor with a Reynolds number in the range of 2900 to 8700. In a certain embodiment, the cross-sectional shape of each roughness element is a chamfer with a chamfer angle of 60 degrees.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

Glossary of Claim Terms

Catalyst Surface: is the surface of the photocatalytic reactor where the photoreaction takes place.

Photocatalytic Reactor: is a device capable of acceleration of a photoreaction in the presence of a catalyst.

Roughness Element: is a member extending from a surface that results in the surface not being smooth.

Relative Height (e/h): is the ratio of height of the roughness element over the height of the duct.

Pitch Ratio (p/e): is the ratio of the pitch over the height of the roughness element. The pitch is the distance between the same points on two different roughness elements.

Relative Width (w/e): is the width of the roughness element over the height of the roughness element.

Roughness Width to Channel Height Ratio (w/h): is the width of the roughness element over the height of the duct.

Reynolds Number (Re): is the ratio of inertial forces to viscous forces for a given flow.

As contemplated by the current invention, artificial roughness elements on a catalyst surface will lead to an enhancement in turbulence intensity, resulting in increased mass transfer and hence, an improved rate of photocatalysis. The optimum pitch ratio is determined to be 10 for all shapes of roughness elements to maximize the turbulence intensity. To enhance the turbulence intensity close to the catalyst surface of the photoreactor channel, a relative height of 0.05 is determined to be optimum for all roughness elements shapes. The isosceles triangle shape of roughness with a bottom angle of 75 degrees is considered the best shape in the studied roughness elements.

Experiment for Turbulence Intensity with Roughness Patterns

Figure 1:
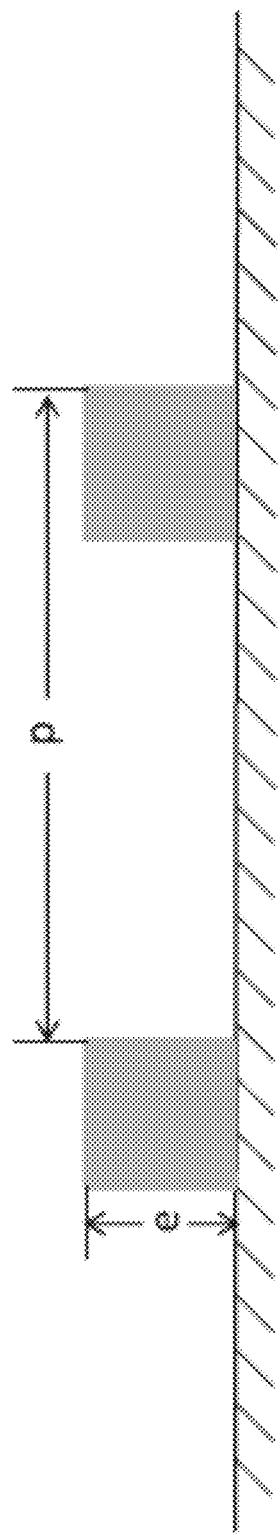
FIG. 1 depicts the representations of 'p' and 'e' when considering a p/e ratio of roughness elements.
Figure 2A:
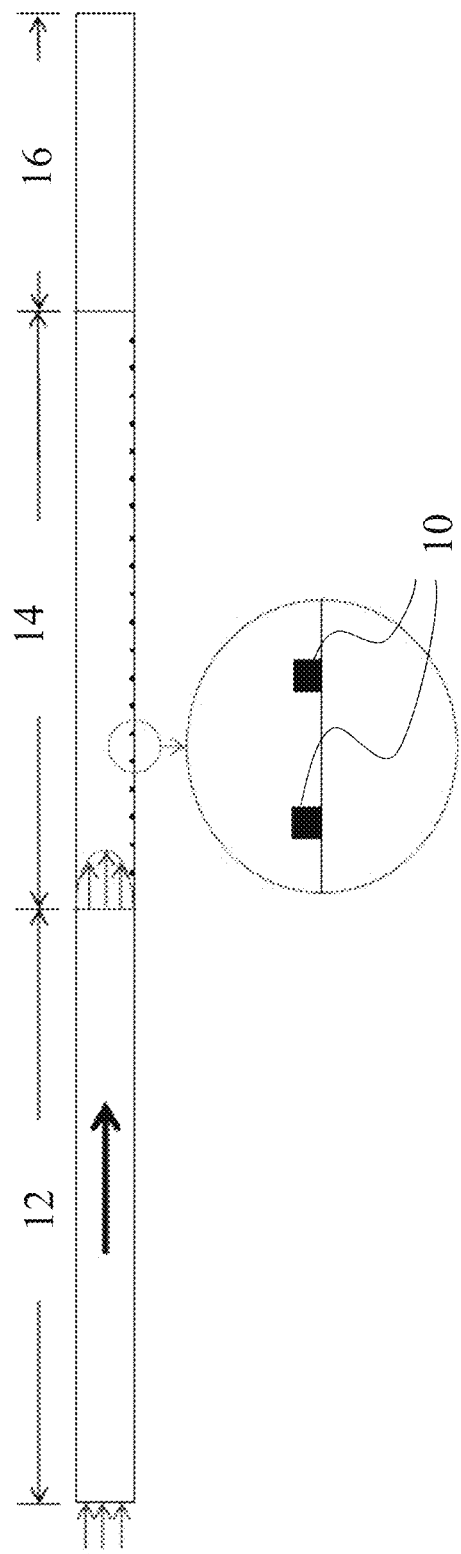
FIG. 2A is an illustration of a photoreactor channel with surface roughness elements on the bottom wall of the test section.

The photoreactor passage was assumed to be a rectangular duct with a cross-section of 2.54×12.7 cm (1×5 in, H×W), and length (L) of 63.5 cm (25 in). A two-dimensional (2D) photoreactor passage with transverse ribs was analyzed to save computer memory and computational time. As shown in FIG. 2A, the passage was divided into three parts: inlet section 102, test section 104, and outlet section 106. The inlet and outlet sections are smooth to reduce the end effects on the test section. The lengths of the inlet, test, and outlet sections are 25.4, 25.4, and 12.7 cm (10, 10, and 5 in), respectively. The height of the passage is 2.54 cm (1 in). The roughness elements 100 are on the bottom surface of the test section.

TABLE 1

The different ranges of parameters of the studied roughness element.

| Study content | Shapes | e/h | p/e | w/h | w/e | α | φ |
|---|---|---|---|---|---|---|---|
| Pitch Ratio |  | 0.05 | 2-20 | 0.02 for chamfered | 0.4 for chamfered | 75° for triangle | 45° for triangle |
| Height |  | 0-0.2 | 10 | 0.01 | — | — | — |
| Triangle | 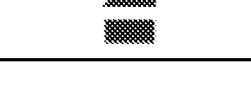 | 0.05 | 10 | — | — | 15°-89° | — |
| Chamfered | 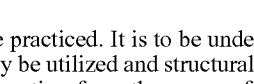 | 0.05 | 10 | 0.02 | 0.4 | — | −60°-60° |
| Rectangle |  | 0.05 | 10 | 0.001-0.2 | 0.2-4 | — | — |

Figure 2B:
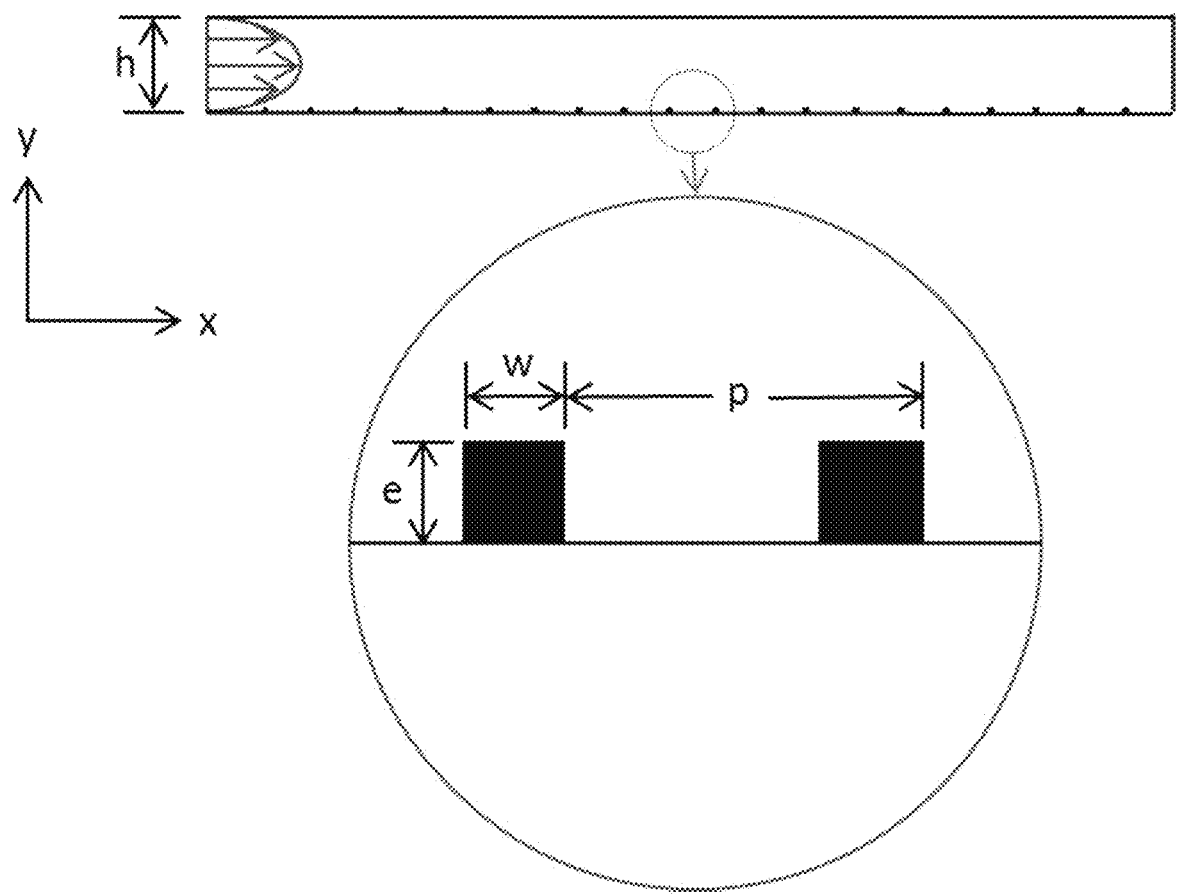
FIG. 2B is a close up of the test/reactor section and the roughness elements along with identifying dimensions.
Figure 3:
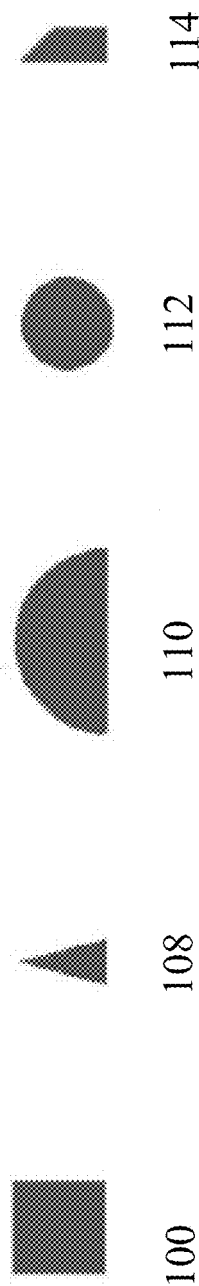
FIG. 3 is an illustration of five different shapes of roughness elements studied in the experiment.

Five different shapes for the roughness element were studied to ascertain the optimum size, shape, and arrangement (See FIG. 3). The five shapes included square 100, triangle 108, semiround 110, Round, 112, and chamfered 114. The roughness elements were placed on the bottom wall of the reactor channel where the catalyst is coated (See FIG. 2). The different ranges of roughness parameters are summarized in Table 1. FIG. 2B provides further clarification as to the meaning of the terms/parameters, where 'e' is the roughness element height, 'p' is the roughness pitch, 'w' is the roughness width, 'h' is the reactor channel height, 'y' is the position in the y direction, and 'x' is the position in the at x direction.

A 2D analysis of airflow through the rectangular duct with transverse rib roughness was carried out using the commercially available CFD software ANSYS Fluent 13.0. The following assumptions were made in the mathematical model: a) the flow is steady, fully developed, and turbulent; and b) the working fluid, air, is incompressible under the operating conditions. Velocity-inlet has been considered as the inlet boundary condition and pressure outlet as the outlet boundary condition in the ANSYS Fluent. The range of Reynolds number (Re) was considered from 2900 to 8700. Thus, the average airflow rate varies from 1 to 3 m/s, as calculated from the Reynolds number. The boundary condition of the outlet pressure is equal to the atmospheric pressure, and no slip wall boundary conditions are used for the analysis. The second order upwind numerical scheme and SIMPLE algorithm are used to discretize the governing equations. A residual value equal to $10^6$ was applied for the resulting calculation convergence. The magnitude of the turbulence intensity in the duct was studied to understand how the different shapes, sizes, and arrangements of the roughness affect the airflow.

The "realizable k-epsilon (k-ε)" model with enhanced wall treatment was employed for the solution of the turbulent momentum equations. The k-epsilon (k-ε) model was chosen based on its simplicity, reasonable accuracy, and wide applicability to different flow conditions [38-41]. The enhanced wall treatment extends the validity of the near-wall modeling beyond the viscous sub layer.

As mentioned before, the effects of five different shapes of roughness elements were investigated at different Reynolds numbers. The magnitude of the turbulence intensity was numerically determined for various relative height (e/h) and pitch ratios (p/e) for the five different shapes of roughness elements. The aim was to find the optimum relative height (e/h), pitch ratio (p/e), and shape of the roughness elements, which would lead to a maximum enhancement of the turbulence intensity in the reactor channel and also an optimum localization of the turbulence intensity close to the catalyst surface. A similar channel with no roughness elements on the walls was also simulated for comparison. For the smooth channel, the magnitude of the turbulence intensity is equal to 8.30% and 15.74% for the Reynolds numbers 2900 and 5800, respectively.

Figure 4:
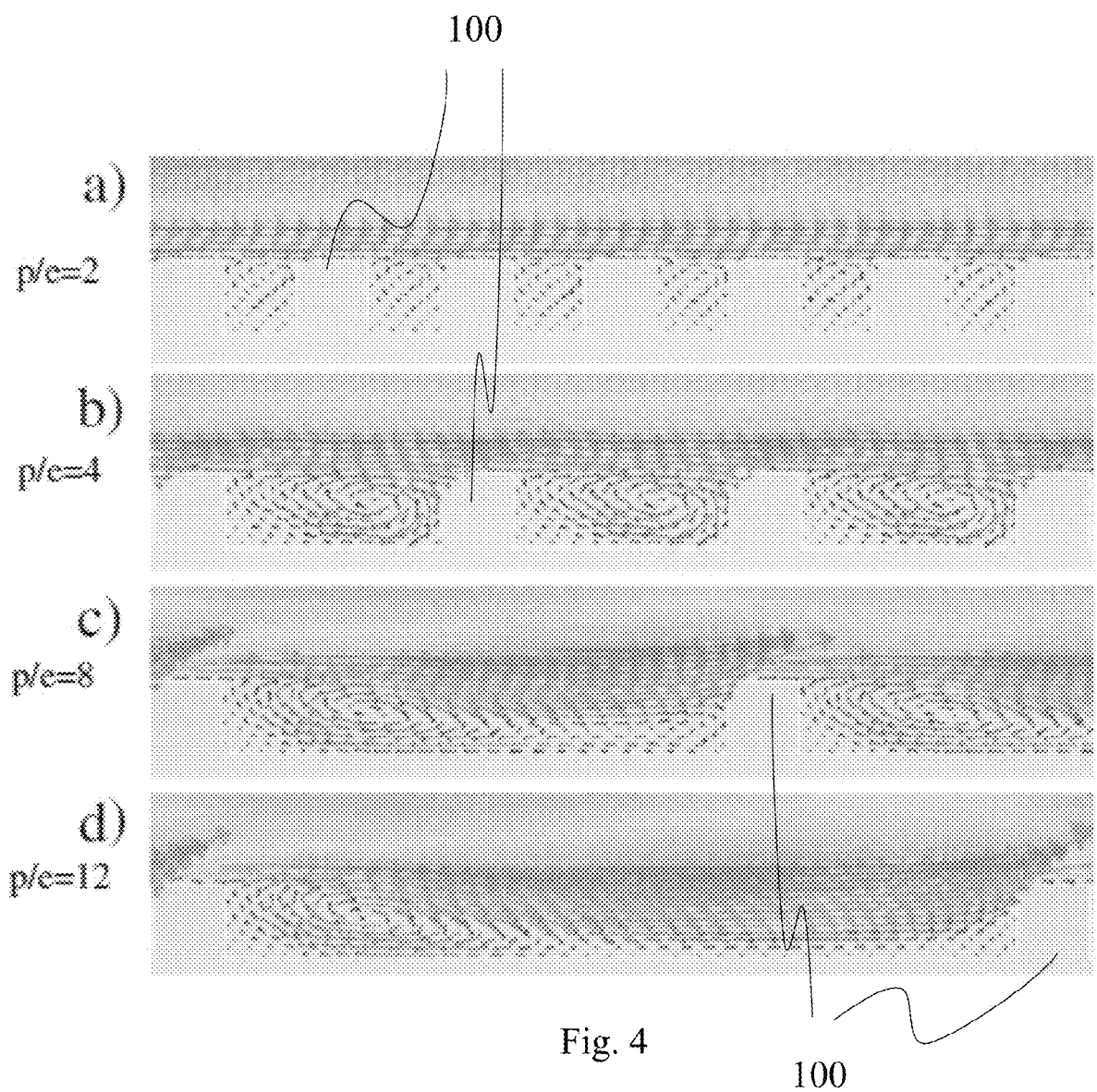
FIG. 4 is a flow simulation of square roughness elements with different pitch ratios.
Figure 5:
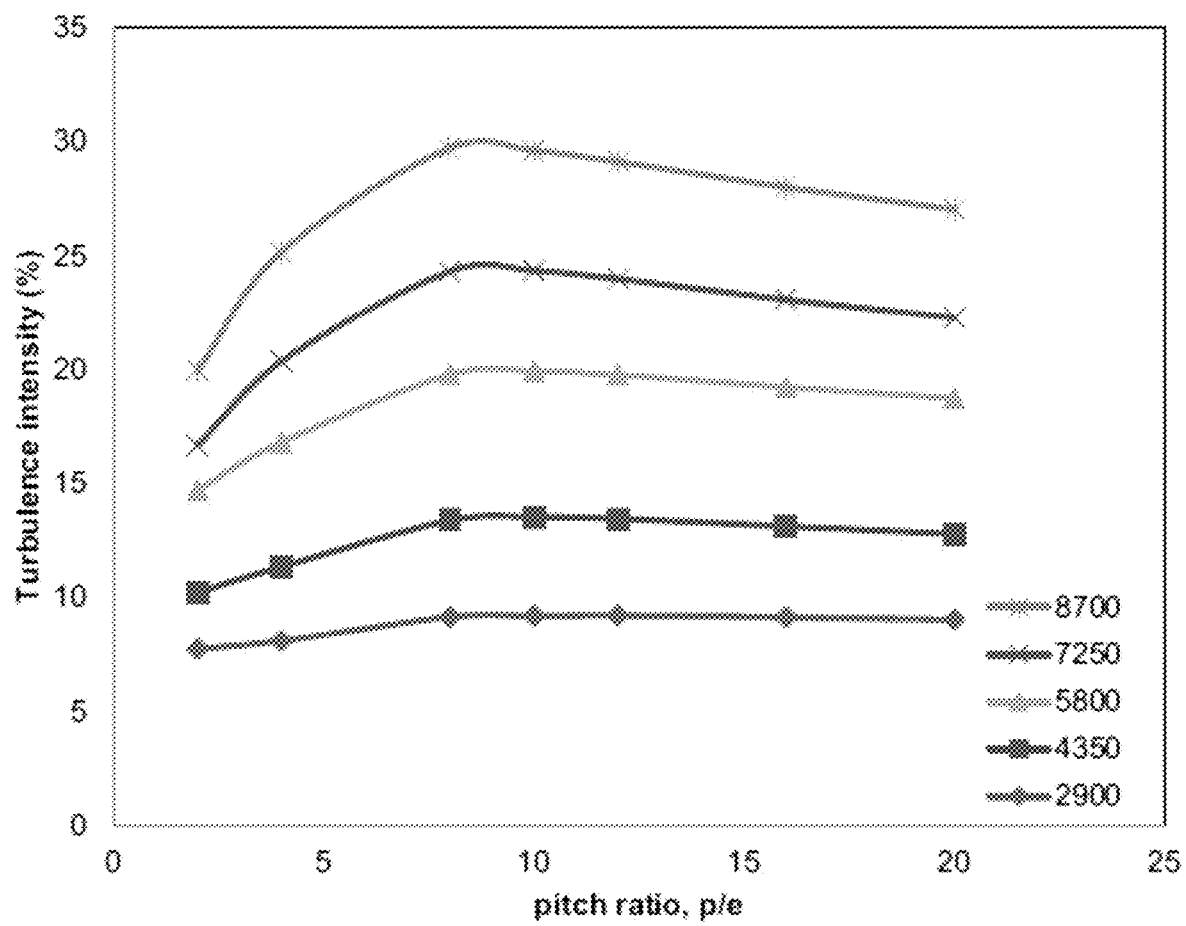
FIG. 5 is a graphical illustration of the effect of square roughness pitch ratio (p/e) on turbulence intensity for Reynolds Number (Re) from 2900 to 8700.

FIG. 4 shows the flow pattern of square roughness elements 100 with pitch ratios from 2 to 12. When the pitch ratio is less than 4 (d-type roughness), the outer flow is observed "riding" over the roughness elements with a separated recirculating region contained between each rib pair. On the other hand, when the pitch ratio is greater than 4 (k-type roughness), reattachment occurs between subsequent ribs. The results agree with those of references [27, 30]. Different pitch ratios with different Reynolds numbers from 2900 to 8700 (average airflow rates from 1 to 3 m/s) are applied in the simulation of the channel with square roughness elements on the wall. The results are summarized in FIG. 5. When the pitch ratio is equal to 10, the magnitude of the turbulence intensity reaches a maximum for all Reynolds numbers. Thus, the optimum pitch ratio would be 10 for any Reynolds number. In this study, Reynolds numbers of 2900 and 5800 (corresponding to average airflow rates of 1 and 2 m/s) were chosen for the photoreactor channel geometry optimization.

In order to study the effect of the height of the roughness elements on the turbulence intensity in the channel, a rectangle was chosen as the representative shape of roughness. The ratio of roughness width to channel height (w/h) was kept at 0.01 and the pitch ratio (p/e) was kept at 10. The width of the roughness element is parallel to the airflow. The number of roughness elements was reduced with an increase in the height of roughness since the pitch ratio (p/e) is kept at 10. Different heights of roughness (e/h) from 0 to 0.2 were investigated with the roughness of 0 corresponding to a smooth channel. The results are summarized in FIG. 6.

Figure 6:
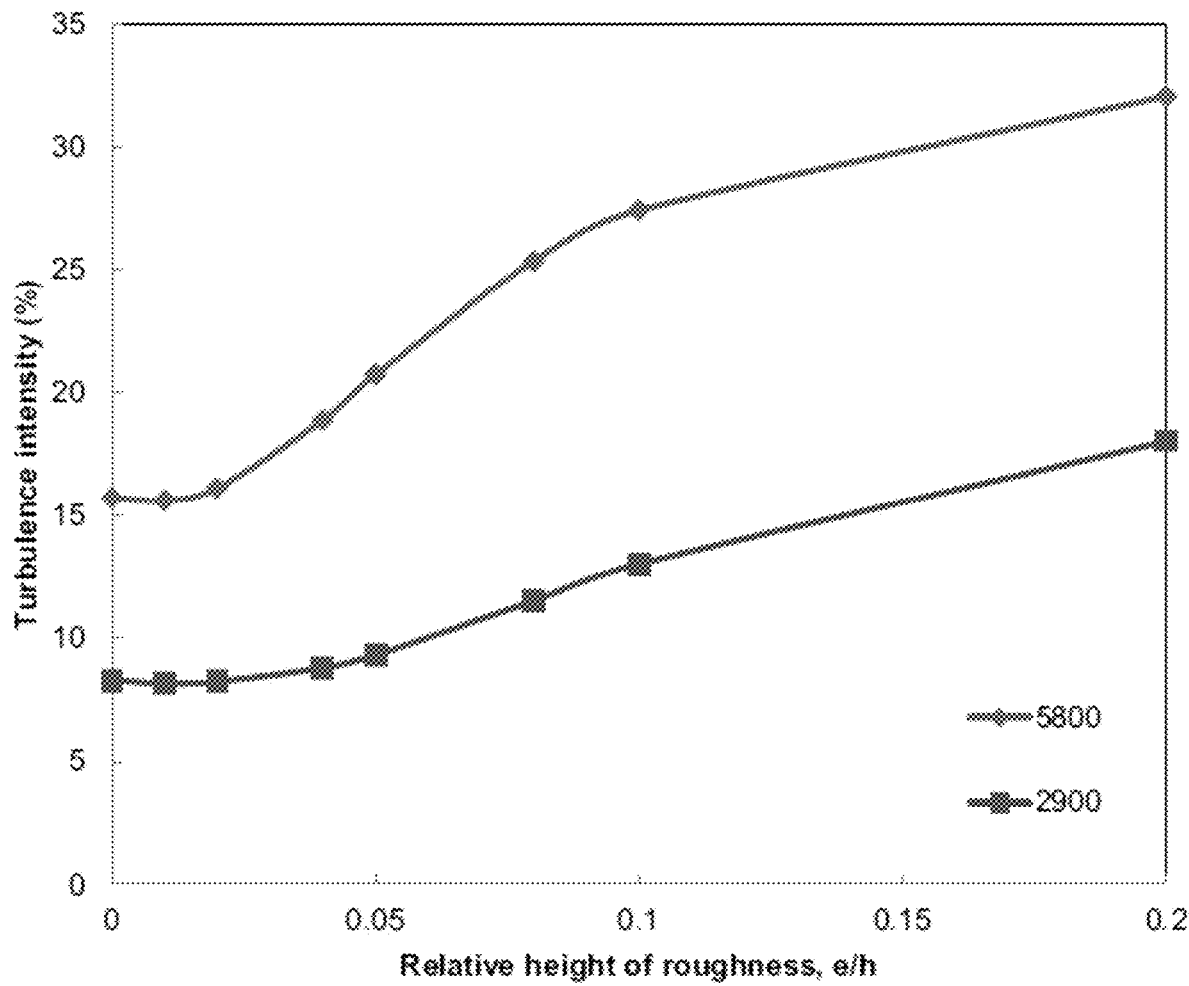
FIG. 6 is a graphical illustration of the effect of height of roughness for Re equal to 2900 and 5800.

FIG. 6 shows that the turbulence intensity is almost constant for relative heights (e/h) less than 0.01 and 0.02 for the Reynolds numbers of 5800 and 2900, respectively. This is because the heights of the roughness elements are less than the flow boundary sublayer and do not affect the flow [42]. On the other hand, when the relative height (e/h) is larger than 0.02, the magnitude of the turbulence intensity increases greatly with an increase in the height of the roughness. However, for a photocatalytic reactor channel, an optimal height of the roughness would be one, which leads to the maximum enhancement in the turbulence intensity near the catalyst surface where the reaction occurs. Thus, it is important to not only enhance the turbulence intensity in the overall channel, but also near the catalyst surface.

Figure 7:
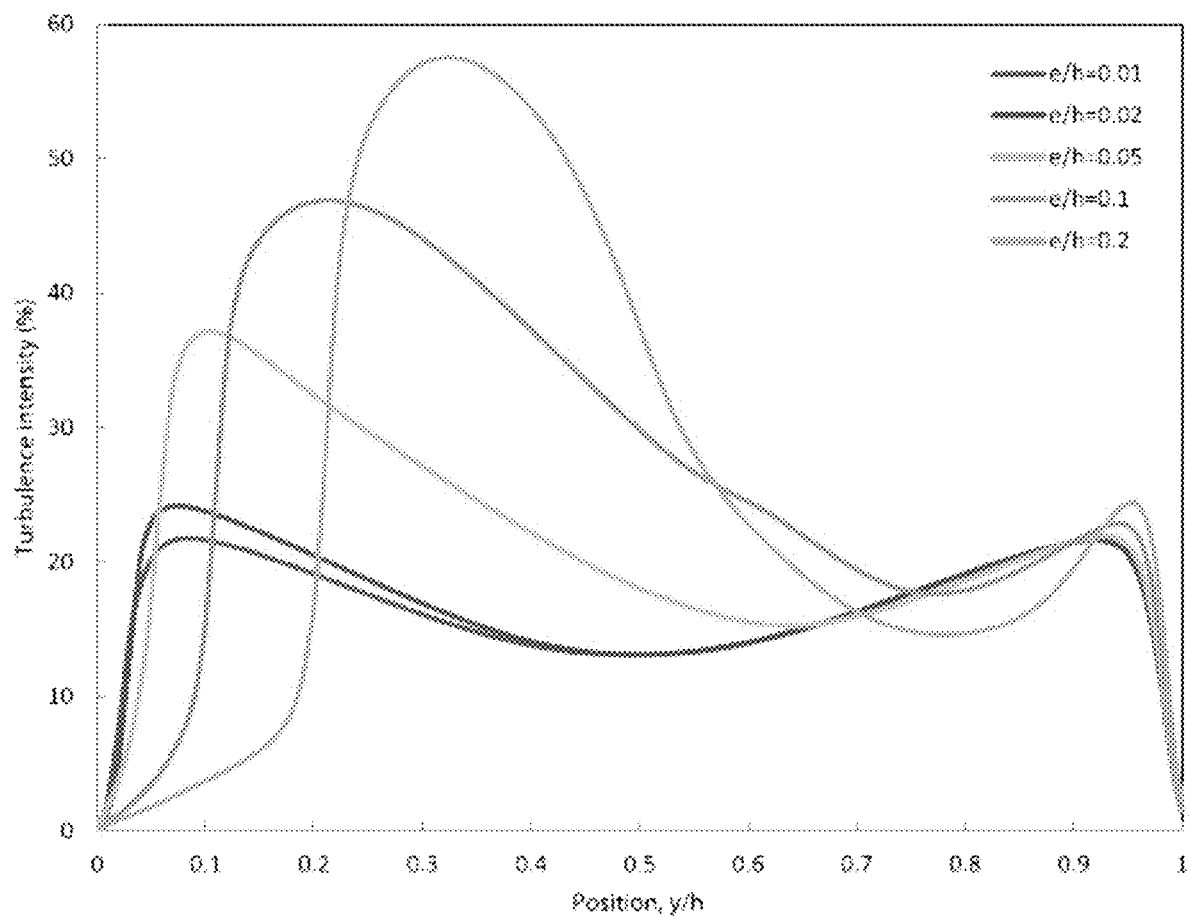
FIG. 7 is a graphical illustration of the magnitude of the average turbulence intensity in the Y-axis direction with different roughness height (Re=5800).

FIG. 7 plots the variation of the turbulence intensity with the distance from the surface for different roughness heights for a Reynolds number of 5800. It is clear that even though an increase in the roughness element height leads to a large increase in the turbulence intensity in the channel, the turbulence intensity close to the catalyst surface (y/h<0.1) is reduced (See FIG. 7). This happens because at higher values of relative roughness height, the reattachment of the free shear layer might not occur [43]. In photocatalysis, it is important to enhance the turbulence close to the catalyst surface, where the reaction is taking place. Assuming that y/h<0.1 is the space where there is significant impact to the mass transfer of the reactants to catalyst surface, see FIG. 7, a relative height (e/h) of 0.05 gives the highest turbulence intensity. Therefore, in this study, the optimum relative height of roughness (e/h) was considered to be 0.05.

Figure 8:
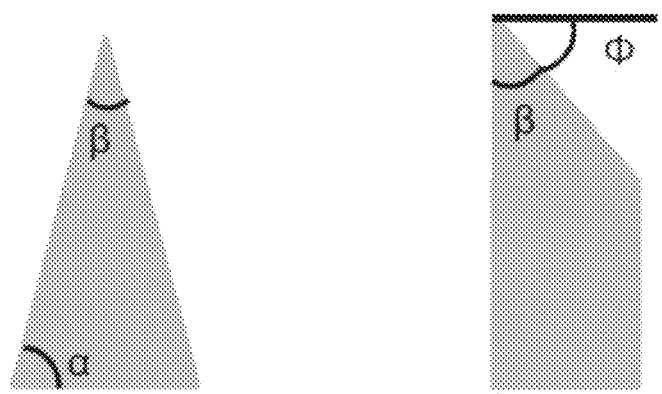
FIG. 8 is an illustration of roughness element shaped as an isosceles triangle and a roughness element having a chamfer shape.
Figure 9A:
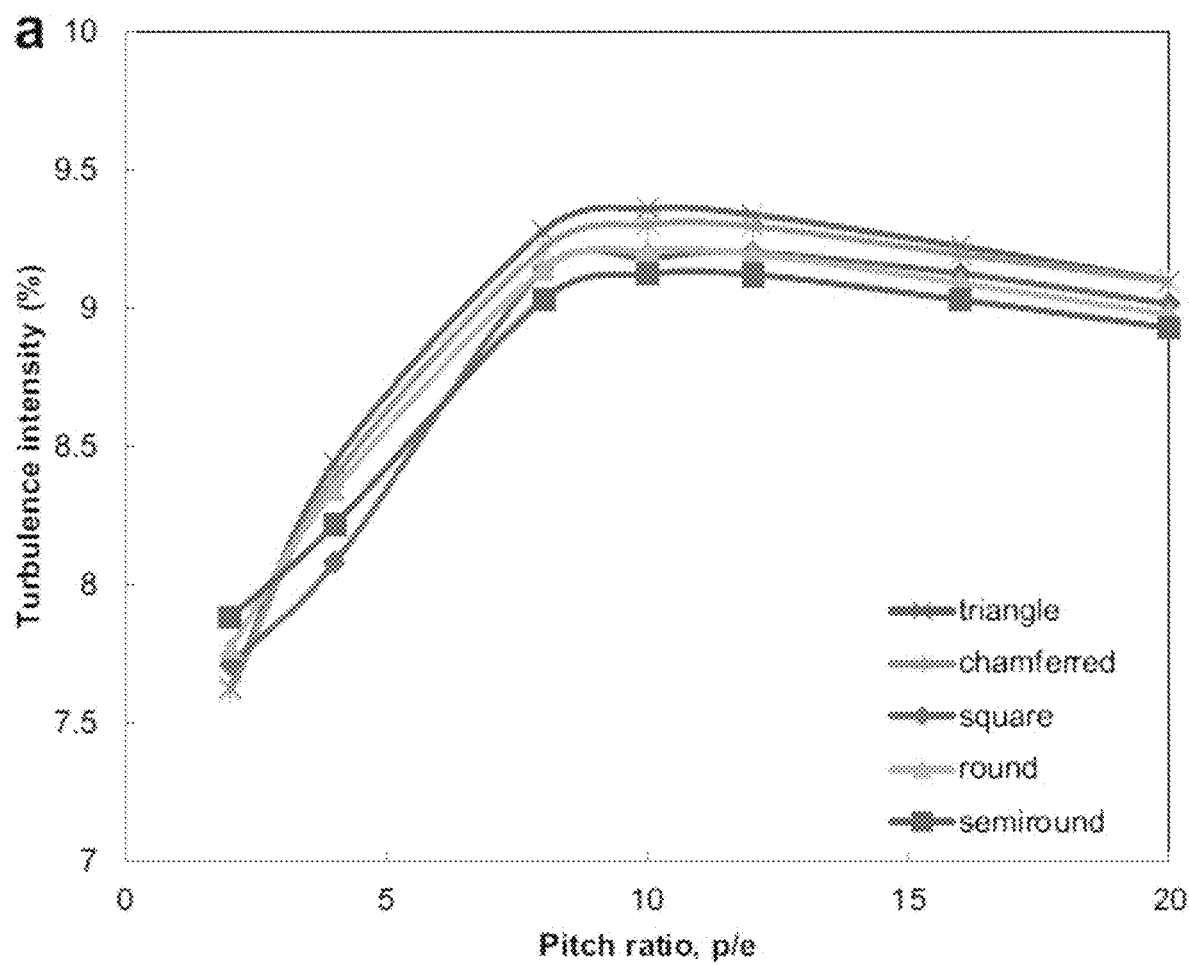
FIG. 9a is a graphical illustration of the effect of different shapes of roughness in the channel for Re=2900.
Figure 9B:
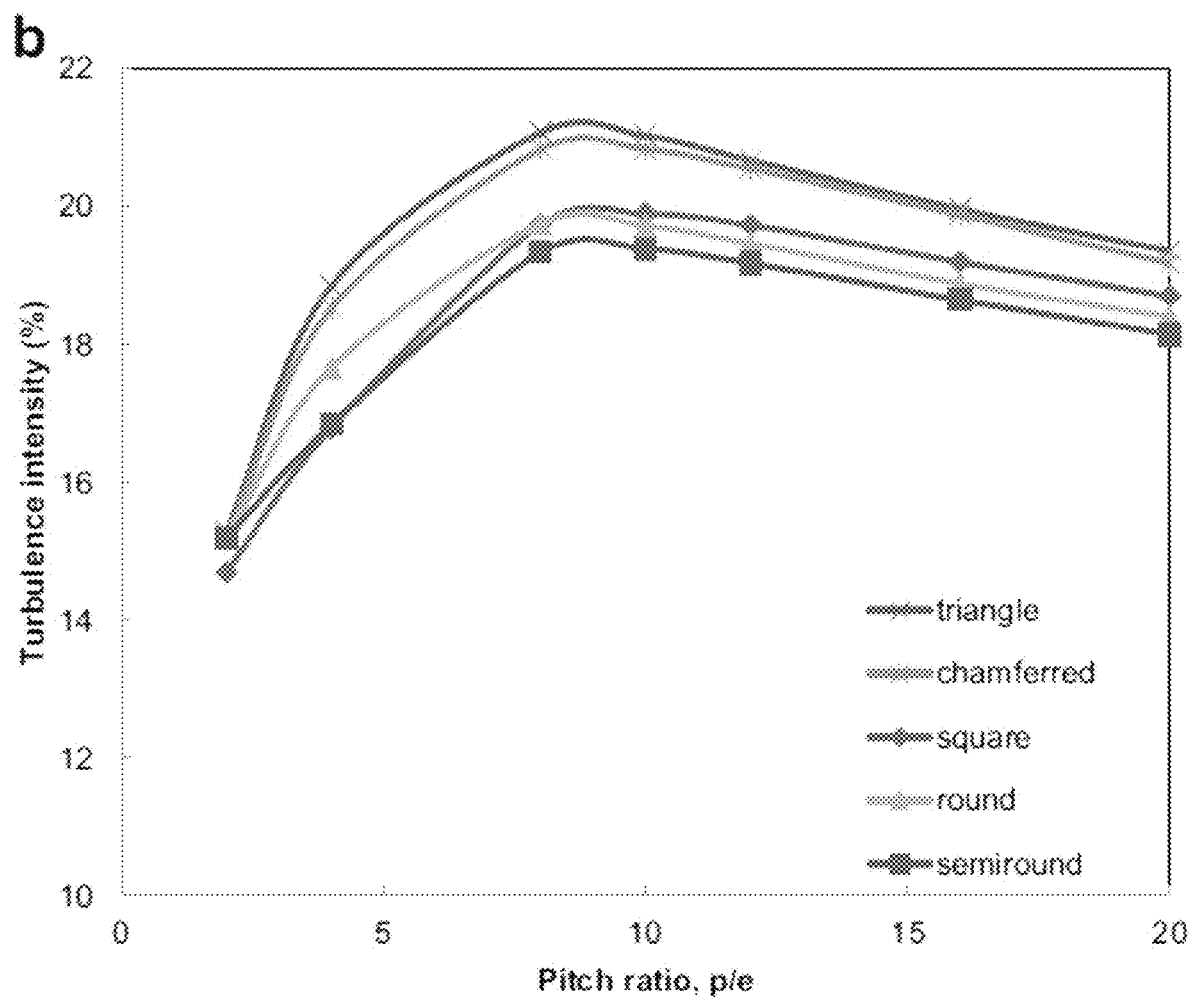
FIG. 9b is a graphical illustration of the effect of different shapes of roughness in the channel for Re=5800.

Roughness pitch ratios (p/e) from 2 to 20 were investigated to study the effect of pitch ratio along the flow direction on turbulence intensity. In addition, different roughness shapes (square, isosceles triangle, semi-round, round, and chamfered shape) were introduced in the reactor channel (See FIG. 3) to find the optimum shape. The relative roughness height (e/h) was kept at 0.05 for all shapes. For the isosceles triangle shape, the base angle (equal to the flow attack angle) α was kept as 75 degrees. For the chamfered shape, the chamfer angle (Φ) was kept as 45 degrees (See FIG. 8). The results are summarized in FIGS. 9a and 9b for Reynolds numbers of 2900 and 5800, respectively.

It is evident that the turbulence intensity reaches a maximum for all shapes of roughness when the pitch ratio is equal to 10. Thus, the optimum pitch ratio was 10 for all shapes of roughness. Among these shapes of roughness, the isosceles triangle shape produces the greatest turbulence intensity in the reactor channel, followed by the chamfered, square, round, and semi round shape, respectively. Since the magnitude of the turbulence intensities is almost the same for the triangle and chamfered shapes of roughness elements, the optimum shape of roughness could be either triangle or chamfered. However, the isosceles triangle may be chosen since it produces less shade than the chamfered shape when the light source is applied from the top of roughness elements. The triangle and chamfered shapes of roughness, shown in FIG. 9, are specific types in that the triangle bottom angle α is equal to 75 degrees and the chamfer angle Φ is equal to 45 degrees. The square roughness element in FIG. 9 is also a specific type of rectangle. The above triangle, chamfered, and rectangle may not be the best shapes and further optimization studies may be required.

To optimize the triangle shape of roughness, the relative height (e/h) was kept as 0.05 and the pitch ratio (p/e) was kept as 10. Base angles (same as flow attack angle) α varying from 15 degrees to 89 degrees were investigated (See FIG. 8). The results are summarized in FIG. 10 for the flow Reynolds numbers of 2900 and 5800, respectively.

Figure 10:
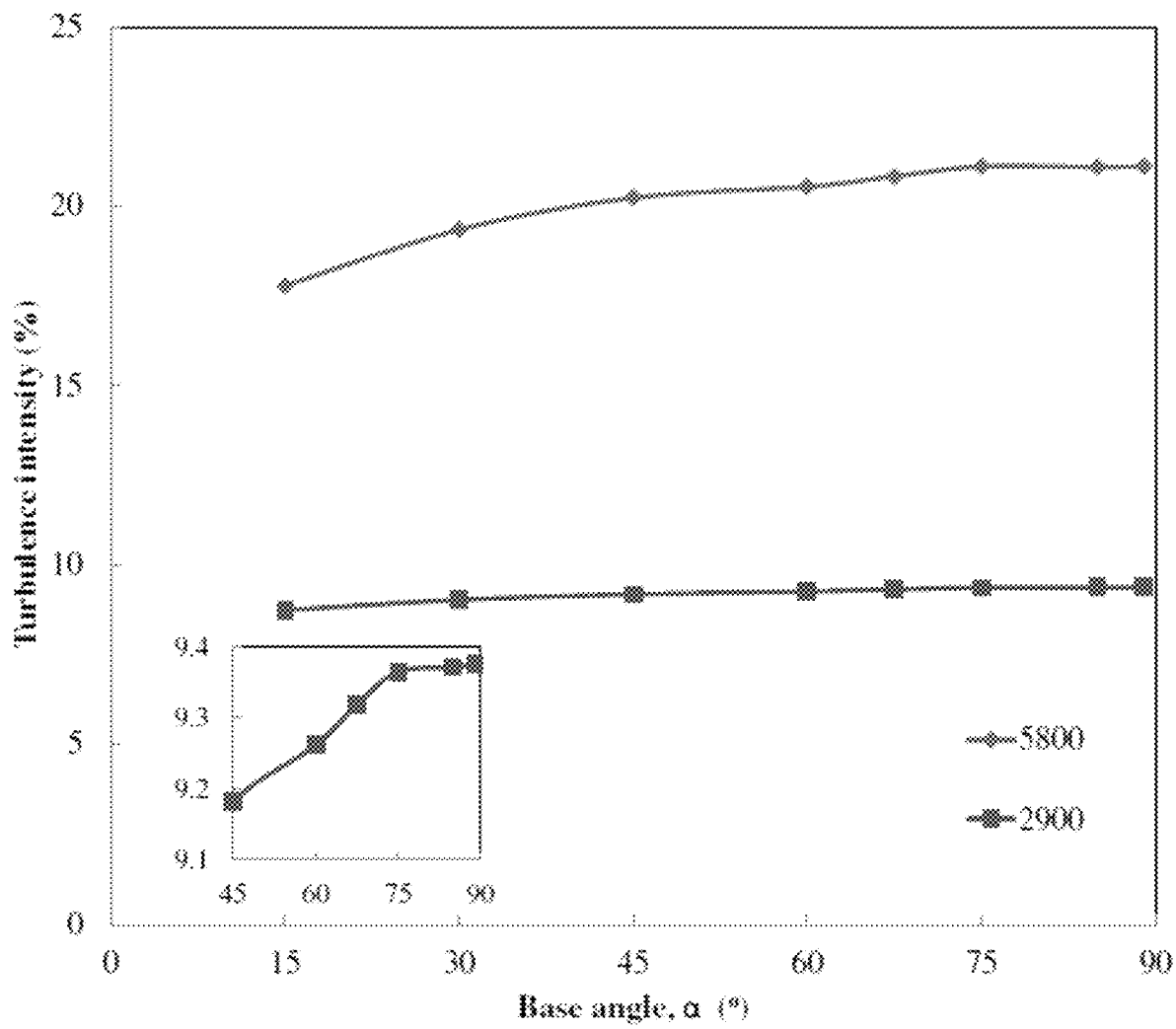
FIG. 10 is a graphical illustration of the effect of base angle of isosceles triangle shape roughness for the roughness number at 2900 and 5800.

From FIG. 10, it can be seen that the magnitude of the turbulence intensity increases with the base angle (a) for both of the Reynolds numbers for the base angles less than 75 degrees. However, from 75 degrees to 89 degrees, the magnitude of the turbulence intensity is almost constant. Thus, the optimal isosceles triangle base angle (α) was chosen as 75 degrees in this study. The magnitudes of turbulence intensity for the optimum triangle shape of roughness (bottom angle equal to 75 degrees) are 9.36% and 21.09% for the Reynolds numbers of 2900 and 5800, respectively.

To optimize the rectangle shape of roughness, the relative height of roughness (e/h) was kept as 0.05 and the pitch ratio (p/e) was kept as 10. For the chosen height and pitch, different relative widths of roughness (w/e) from 0.2 to 4 were investigated. The results are summarized in FIG. 11 for the Reynolds numbers of 2900 and 5800, respectively.

Figure 11:
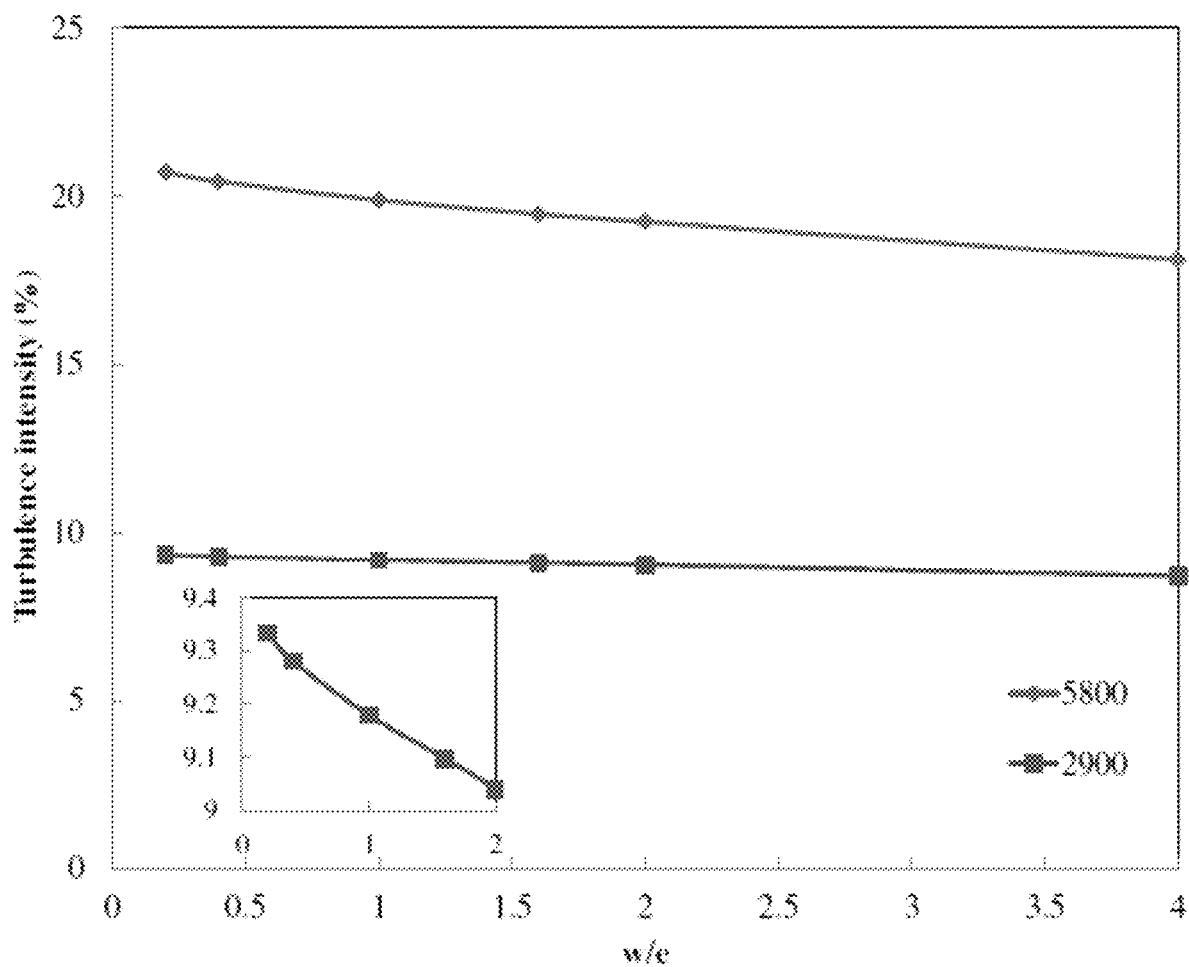
FIG. 11 is a graphical illustration of the effect of relative width (w/e) on rectangle roughness for the Re at 2900 and 5800.

According to FIG. 11, the magnitude of turbulence intensity decreases when the roughness width increases for both of the Reynolds number 2900 and 5800. The results indicate that the roughness width should be kept as small as possible. The optimum roughness relative width was chosen as 0.02 in this study. The turbulence intensities are 9.33% and 20.73% corresponding to the Reynolds numbers of 2900 and 5800, respectively.

Under conditions similar to those mentioned above, the relative height of roughness (e/h) was kept at 0.05, the pitch ratio (p/e) was kept at 10, and the relative width of roughness (w/e) was kept at 0.4. Different chamfer angles (Φ) from −60 degrees to 60 degrees were investigated. The negative angles correspond to the flow attack at the chamfer side; the positive angles correspond to the flow attack at the backside of the chamfer, and the zero angles correspond to the rectangle roughness. The results are summarized in FIG. 12 for the flow Reynolds number equal to 2900 and 5800, respectively.

Figure 12:
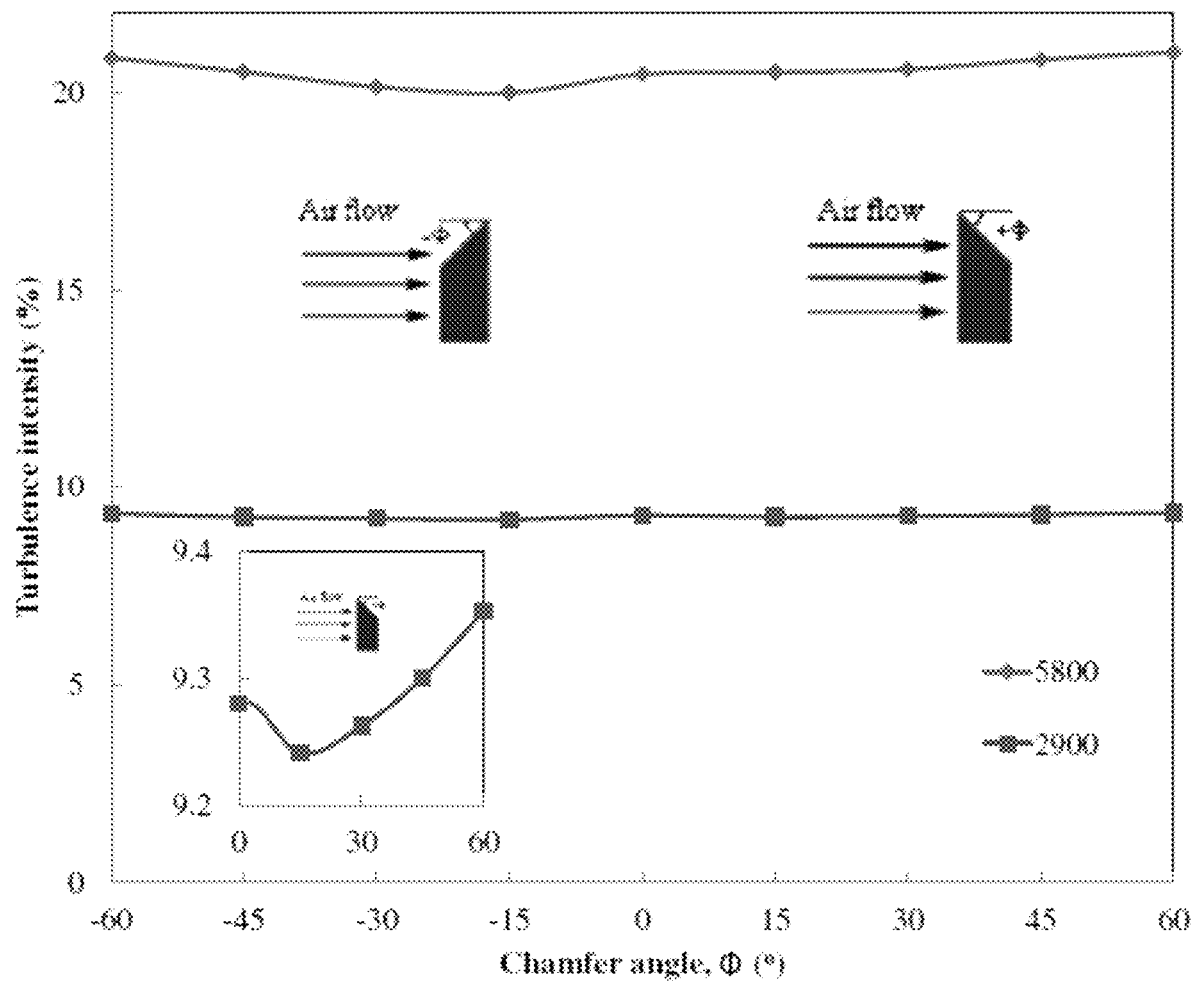
FIG. 12 is a graphical illustration of the effect of chamfer angle of chamfer shape roughness for the Rey at 2900 and 5800

From FIG. 12, the magnitude of the turbulence intensity increases when the chamfer angle (Φ) is larger than the absolute value of 15 degrees. The magnitude of the turbulence intensity may keep increasing when the absolute value of the chamfer angle is larger than 60 degrees. However, as mentioned before, the roughness might be difficult to construct in a practical reactor if the zenith angle (β) is too small since a larger chamfer angle (Φ) leads to a smaller zenith angle (β). From FIG. 12, the magnitude of the turbulence intensity of flow attack at the back side of the chamfer (+Φ) is obviously larger than flow attack at the chamfer side (−Φ). Thus, the optimal chamfer angle (Φ) is chosen as 60 degrees for the photoreactor channel in this study. The magnitudes of turbulence intensities for the optimum chamfer shape roughness (Φ=60 degrees) are 9.35% and 21.02% for Reynolds numbers of 2900 and 5800, respectively.

Table 2 summarizes the optimal parameters for different shapes of roughness. When the chamfer angle (Φ) is increased, the zenith angle (β) of the chamfered shape is decreased (See FIG. 8). This means the magnitude of the turbulence intensity is increased when the zenith angle (β) of the chamfer is decreased. This result is quite similar with the triangle shape of roughness. From the results of these shapes of roughness elements, it may be concluded that, in general, under similar conditions, the roughness elements with a smaller top width (or zenith) is typically better for increasing the turbulence intensity in the channel independent of the shape. This rule could be used to choose the shape of the roughness element for enhancing the magnitude of turbulence intensity in a reactor duct.

TABLE 2

Summary of the optimal parameters for different shapes of roughness elements.

|  | Rectangle | Triangle | Round | Semiround | Chamfered | Smooth |
|---|---|---|---|---|---|---|
| Pitch Ratio (p/e) | 10 | 010 | 10 | 10 | 10 | — |
| Relative Height (e/h) | 0.05 | 0.05 | 0.05 | 0.05 | 0.05 | 0 |
| Relative Width (w/e) | 0.2 | — | — | — | — | — |
| Zenith angle (β) | — | 30° | — | — | 30° | — |
| Turbulence intensity in optimal parameter (%) | 9.33[a] 20.73[b] | 9.36[a] 21.09[b] | 9.21[a] 19.73[b] | 9.12[a] 19.39[b] | 9.35[a] 21.02[b] | 8.30[a] 15.74[b] |
| Others | Smaller wideth is better | Larger bottom angle or smaller zenith angle is better | — | — | Positive chamfer angle with smaller zenith angle is better | — |

Table 2 shows that the magnitude of the turbulence intensity for the optimal isosceles triangle shape is slightly larger than the optimal chamfered shape. Also, as mentioned before, the isosceles triangle produces less shade than the chamfered shape roughness when the light source is positioned above the roughness elements. Thus, the isosceles triangle with the bottom angle (α) equal to 75 degrees (or β=30 degrees) is considered to be the best shape to maximize the turbulence intensity in the photocatalytic reactor channel fabricated for this experiment.

Figure 13:
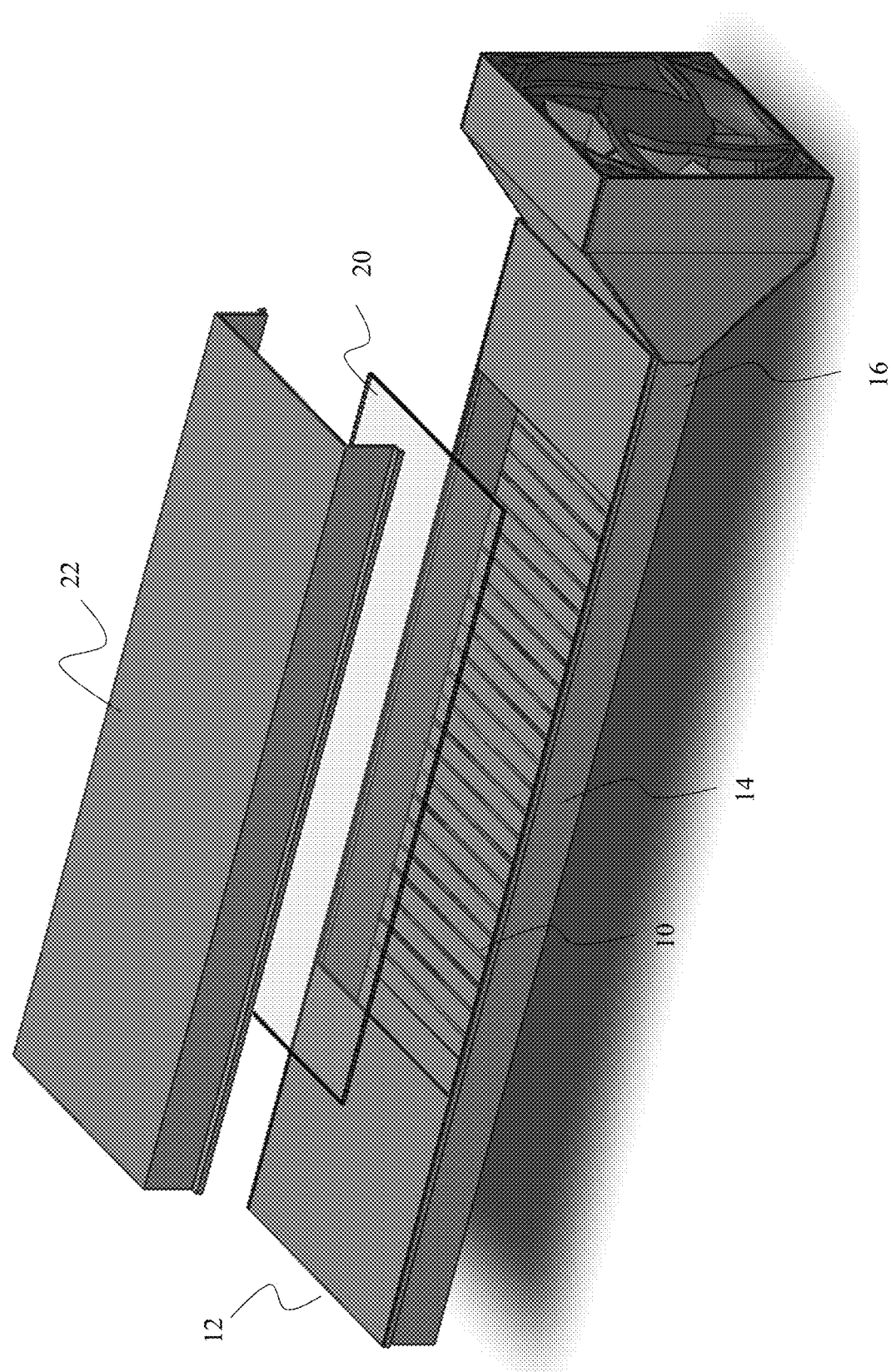
FIG. 13 is a perspective view of an embodiment of a photocatalytic reactor.

Experimental Investigation of Photocatalysis Enhancement with Roughness Patterns An experimental set-up was designed and fabricated to study the effect of surface roughness elements in an air photocatalytic reactor. The experiment was designed to clean the contaminated air in a closed chamber. A plate-type photocatalytic reactor was chosen as the model reactor (See FIG. 13). The experimental duct consists of a channel with a cross section of 2.54×12.7 cm (1×5 in, H×W) and length (L) 50 cm (20 in), which includes three sections, namely, inlet section 12, test section 14, and exit section 16. Both inlet and exit sections are smooth ducts. A catalyst plate with roughness elements 10 was put on the bottom wall of test section 14. In order to keep the same channel height of the inlet, test, and exit sections, smooth plates with the same thickness were also put on the bottom wall of the inlet and exit sections. UV-A transparent glass 20 was used as the lid of test section 14. UV lamp box 22 was placed on the top of the test section 14 as the light source. A 12.7 cm (5 in) DC fan was connected with a transition duct at the exit section to pull the airflow through the reactor (FIG. 13).

A reflective aluminum sheet (0.022 in thick) was used as the material to build the reactor duct. The lamp box includes 5 RPR-3500Ao UV lamps (12 in long). The RPR-3500Ao UV-lamps emit light in a wavelength band between 300 and 420 nm with an approximately Gaussian spectral distribution ($\lambda_{max}$=350 nm). An aluminum plate (0.05 in thick) of 12.7×30.48 cm (5×12 in) size was used as the catalyst support substrate. Transverse ribs were used as the roughness elements on the rough plate (See FIG. 13). From the simulation results, the optimal pitch ratio (p/e) and relative height of roughness (e/h) were found to be 10 and 0.05, respectively. Therefore, the roughness elements for the experimental study were chosen to have the optimum pitch ratio (p/e) and the relative roughness height from the simulation study. Thus, the roughness elements were chosen as 16 AWG (0.05 in diameter) aluminum wires with the distance between two roughness elements as 1.27 cm (0.5 in) which gives the relative height of roughness (e/h) and pitch ratio (p/e) as 0.05 and 10, respectively. The transverse ribs roughness elements were fixed on the aluminum plate by drilling small holes on the edge of the plate and tying a 36 AWG (0.005 in diameter) wire on it. The photocatalyst was spray coated on the roughness plate. The catalyst, which was sprayed on the plate, is 250 mg Degussa P25 titanium dioxide (FIG. 14*b*). A smooth catalyst plate, which was coated with the same amount of catalyst, was also made for comparison.

As mentioned before, the reactor was designed to clean the contaminated air in a closed chamber. The specifications of the reactor and the parameters used in the investigation are given in Table 3. The chamber was a 604 L (32×32×36 in) cubic box. The average UV intensity on the catalyst plate was measured by an EPPLEY UV radiometer (290-385 nm) and was determined to be 100 W/m². The airflow rate was regulated by changing the voltage of the DC fan and measured by an ALNOR RVA801 anemometer at the inlet side. The experiment was carried out at room temperature and 50% relative humidity. Toluene was chosen as the representative air contaminant. A concentration of 1 ppm was obtained by evaporating 2.6 ml of liquid toluene in the chamber. The concentration of toluene in the chamber was measured by a gas chromatograph (GC) with FID detector.

Figure 14:
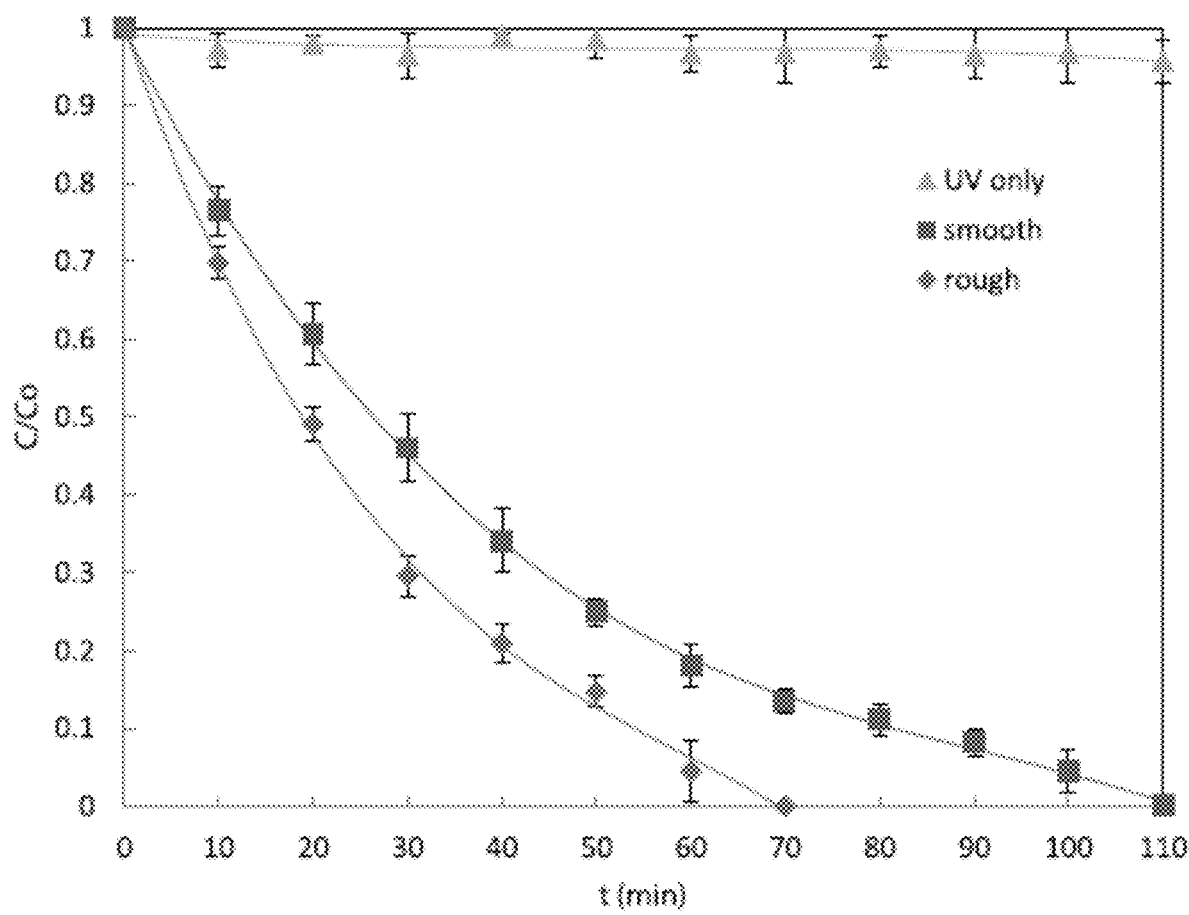
FIG. 14 is a graphical illustration of a comparison of the photocatalytic reactor performance for reactors with a smooth catalyst surface and a catalyst surface with a roughness pattern (Contaminant: 1 ppm toluene; Re: 2900; error bars represent standard deviations for three tests).

FIG. 14 shows the experimental results, which compares the photocatalytic performance of the reactor with a smooth catalyst surface and a rough catalyst surface. For comparison, a plate without a coated catalyst was also studied under the same conditions (same UV intensity and Reynolds number). The results show that toluene is not photo decomposed under just UV irradiation. From FIG. 14, it is seen that the photocatalytic reactor with a rough catalyst surface takes 70 min to clean 1 ppm toluene in a 604 L closed chamber compared to 110 min for a reactor with a smooth catalyst surface. This is a significant improvement in the reactor performance in reducing the air cleaning time. The enhanced reactor performance is due to the roughness elements that were shown from the simulation study to increase the turbulence intensity. From simulation results, when the Reynolds number is equal to 2900, the turbulence intensity for a smooth channel and a round transverse rib rough channel is 8.30% and 9.21%, respectively (See Table 2). Thus, a 0.91% increase in the magnitude of the turbulence intensity produces about 36% improvement in the reactor performance.

The reaction surface area for a rough surface is higher than a smooth surface, which would enhance the photocatalytic performance. Although the surface area of a rough surface is generally larger than a smooth surface, the rough surface has more shadow or receives less photons near the roughness elements as compared to a smooth surface. The catalyst surface with shadow usually plays a less important role in the photocatalysis process. In addition, the increase in the catalyst surface area of a rough plate is small (only around 5% larger area for a rough plate as compared to a smooth plate). Thus, the contribution of the increased reaction surface area of a rough plate in the photocatalytic process was not considered in this study.

REFERENCES

[1] Austin B S, Greenfield S M, Weir B R, Anderson G E, Behar J V. *Modeling the indoor environment*. Environ Sci Technol 1992; 26:851-8.

[2] Jones A P. *Indoor air quality and health*. Atmos Environ 1999; 33:4535-64.

[3] Begum B A, Paul S K, Hossain M D, Biswas S K, Hopke P K. *Indoor air pollution from particulate matter emissions in different households in rural areas of Bangladesh*. Building Environ 2009; 44.

[4] Gupta S, Khare M, Goyal R. *Sick building syndrome—a case study in a multistory centrally air-conditioned building in the Delhi City*. Building Environ 2007; 42.

[5] Kolarik J, Toftum J. *The impact of a photocatalytic paint on indoor air pollutants: sensory assessments*. Building Environ 2012; 57.

[6] Zhang Y, Ram M K, Stefanakos E K, Goswami D Y. *Synthesis, characterization, and applications of ZnO nanowires*. J Nanomater 2012; 2012.

[7] Goswami D Y, Trivedi D M, Block S S. *Photocatalytic disinfection of indoor air*. J Sol Energy Eng-Trans ASME 1997; 119:92-6.

[8] Dibble L A, Raupp G B. *Fluidized-bed photocatalytic oxidation of trichloroethylene in contaminated airstreams*. Environ Sci Technol 1992; 26:492-5.

[9] Hossain M M, Raupp G B, Hay S O, Obee T N. *Three-dimensional developing flow model for photocatalytic monolith reactors*. AIChE J 1999; 45:1309-21.

[10] Larson S A, Widegren J A, Falconer J L. *Transient studies of 2-propanol photocatalytic oxidation on titania*. J Catal 1995; 157:611-25.

[11] Obee T N, Brown R T. *TiO2 photocatalysis for indoor air applications-effects of humidity and trace contaminant levels on the oxidation rates of formaldehyde, toluene, and 1,3-butadiene*. Environ Sci Technol 1995; 29:1223-31.

[12] Riffat S B, Zhao X. *Preliminary study of the performance and operating characteristics of a mop-fan air cleaning system for buildings*. Building Environ 2007; 42:3241-52.

[13] Sun R-B, Xi Z-G, Chao F-H, Zhang W, Zhang H-S, Yang D-F. *Decomposition of low-concentration gasphase toluene using plasma-driven photocatalyst reactor*. Atmos Environ 2007; 41:6853-9.

[14] Vohra A, Goswami D Y, Deshpande D A, Block S S. *Enhanced photocatalytic disinfection of indoor air*. Appl Catal B 2006; 64:57-65.

[15] Goswami D Y. *Decontamination of ventilation systems using photocatalytic air cleaning technology.* J Sol Energy Eng-Trans ASME 2003; 125:359-65.
[16] Chen F, Yang X, Mak H K C, Chan D W T. *Photocatalytic oxidation for antimicrobial control in built environment: a brief literature overview.* Building Environ 2010; 45.
[17] Daisey J M, Angell W J, Apte M G. *Indoor air quality, ventilation and health symptoms in schools: an analysis of existing information.* Indoor Air 2003; 13.
[18] Lee S C, Guo H, Li W M, Chan L Y. *Inter-comparison of air pollutant concentrations in different indoor environments in Hong Kong.* Atmos Environ 2002; 36.
[19] Mo J, Zhang Y, Yang R. *Novel insight into VOC removal performance of photocatalytic oxidation reactors.* Indoor Air 2005; 15:291-300.
[20] Passalia C, Martinez Retamar M E, Alfano O M, Brandi R J. *Photocatalytic degradation of formaldehyde in gas phase on TiO2 films: a kinetic study.* Int J Chem Reactor Eng 2010; 8.
[21] Birnie M, Gillott M, Riffat S. *Incorporating mass transfer theory to model continuous flow type photocatalytic reactors for integration into novel low energy ventilation systems.* J Energy Inst 2006; 79.
[22] Queffeulou A, Geron L, Archambeau C, Le Gall H, Marquaire P M, Zahraa O. *Kinetic study of acetaldehyde photocatalytic oxidation with a thin film of TiO2 coated on stainless steel and CFD modeling approach.* Ind Eng Chem Res 2010; 49:6890-7.
[23] Salvado-Estivill I, Hargreaves D M, Puma G L. *Evaluation of the intrinsic photocatalytic oxidation kinetics of indoor air pollutants.* Environ Sci Technol 2007; 41:2028-35.
[24] Yang R, Zhang Y, Xu Q, Mo J. *A mass transfer based method for measuring the reaction coefficients of a photocatalyst.* Atmos Environ 2007; 41:1221-9.
[25] Chen Q, Meng J-A. *Field synergy analysis and optimization of the convective mass transfer in photocatalytic oxidation reactors.* Int J Heat Mass Transfer 2008; 51.
[26] Vohra A. *Photocatalytic disinfection of indoor air: effect of relative humidity and surface roughness of photocatalytic reactor.* University of Florida; 2005.
[27] Perry A E, Schofiel Wh, Joubert P N. *Rough wall turbulent boundary layers.* J Fluid Mechanics 1969; 37:383-413.
[28] Antonia R A, Luxton R E. *Response of a turbulent boundary layer to an upstanding step change in surface roughness.* J Basic Eng 1971; 93:22-33.
[29] Hanjalic K, Launder B E. *Fully developed asymmetric flow in a plane channel.* J Fluid Mechanics 1972; 51:301-35.
[30] Cui J, Patel V C, Lin C L. *Large-eddy simulation of turbulent flow in a channel with rib roughness.* Int J Heat Fluid Flow 2003; 24:372-88.
[31] Wang L, Hejcik J, Sunden B. *PIV measurement of separated flow in a square channel with streamwise periodic ribs on one wall.* J Fluids Eng-Trans ASME 2007; 129:834-41.
[32] Kestin J, Wood R T. *Influence of turbulence on mass transfer from cylinders.* J Heat Transfer 1971; 93:321-7.
[33] Kataoka K, Kamiyama Y, Hashimoto S, Komai T. *Mass-transfer between a plane surface and an impinging turbulent jet—the influence of surface—pressure fluctuations.* J Fluid Mechanics 1982; 119:91-105.
[34] Simonich J C, Bradshaw P. *Effect of free—stream turbulence on heat—transfer through a turbulent boundary—layer.* J Heat Transfer-Trans ASME 1978; 100:671-7.
[35] Varun, Saini R P, Singal S K. *A review on roughness geometry used in solar air heaters.* Sol Energy 2007; 81:1340-50.
[36] Sanitjai S, Goldstein R J. *Effect of free stream turbulence on local mass transfer from a circular cylinder.* Int J Heat Mass Transfer 2001; 44.
[37] Moraveji M K, Sajjadi B, Jafarkhani M, Davarnejad R. *Experimental investigation and CFD simulation of turbulence effect on hydrodynamic and mass transfer in a packed bed airlift internal loop reactor.* Int Commun Heat Mass Transfer 2011; 38:518-24.
[38] Huang Y, Zheng H, Mao W W, Li G H, Ye B. *Numerical simulation of air-soil two-phase flow based on turbulence modeling.* Nat Hazards 2011; 58:311-23.
[39] Ong M C, Utnes T, Holmedal L E, Myrhaug D, Pettersen B. *Numerical simulation of flow around a circular cylinder close to a flat seabed at high Reynolds numbers using a k-epsilon model.* Coastal Eng 2010; 57:931-47.
[40] Feigley C E, Do T H, Khan J, Lee E, Schnaufer N D, Salzberg D C. *Deriving realistic source boundary conditions for a CFD simulation of concentrations in workroom air.* Ann Occup Hyg 2011; 55:410-20.
[41] Kumar S, Saini R P. *CFD based performance analysis of a solar air heater duct provided with artificial roughness.* Renew Energy 2009; 34:1285-91.
[42] Prasad B N, Saini J S. *Optimal thermohydraulic performance of artificially roughened solar air heaters.* Sol Energy 1991; 47:91-6.
[43] Momin A M E, Saini J S, Solanki S C. *Heat transfer and friction in solar air heater duct with V-shaped rib roughness on absorber plate.* Int J Heat Mass Transfer 2002; 45:3383-96.
Yangyang Zhang, Elias K. Stefanakos, D. Yogi Goswami. *Effect of photocatalytic surface roughness on reactors effectiveness for indoor air cleaning.* Building and Environment 61 (2013) 188-196.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A photocatalytic reactor comprising:
 a reactor catalyst surface having a plurality of roughness elements, wherein the reactor catalyst surface has a width perpendicular to a longitudinal axis extending between a fluid inlet end and a fluid outlet end of the reactor catalyst surface;

two or more roughness elements in the plurality of roughness elements having a pitch extending parallel to the longitudinal axis of the reactor catalyst surface and a pitch ratio of 4-20;

each roughness element further including:
- a relative height ratio in a range of 0.01-0.1;
- a relative width ratio in a range of 0.01-4; and
- a cross-sectional shape, wherein the cross-sectional shape is triangular, chamfered, round, or semiround.

2. The photocatalytic reactor of claim 1, further comprising a roughness element width to channel height ratio of 0.01.

3. The photocatalytic reactor of claim 1, further comprising the reactor catalyst surface having a photocatalyst coating.

4. The photocatalytic reactor of claim 1, further comprising the relative width ratio being 0.02.

5. The photocatalytic reactor of claim 1, further comprising a fluid source moving fluid across the reactor catalyst surface, wherein the fluid moving across the reactor catalyst surface has a Reynolds number in the range of 2900 to 8700.

6. The photocatalytic reactor of claim 1, wherein the cross-sectional shape of each roughness element is an isosceles triangle.

7. A photocatalytic reactor comprising:
- a reactor catalyst surface having a plurality of roughness elements, wherein the reactor catalyst surface has a width perpendicular to a longitudinal axis extending between a fluid inlet end and a fluid outlet end of the reactor catalyst surface;
- two or more roughness elements in the plurality of roughness elements having a pitch extending parallel to the longitudinal axis of the reactor catalyst surface and a pitch ratio of 4-20;

each roughness element further including:
- a relative height ratio;
- a relative width ratio in a range of 0.01-4; and
- a cross-sectional shape, wherein the cross-sectional shape is triangular, chamfered, round, or semiround.

8. The photocatalytic reactor of claim 7, further comprising a roughness element width to channel height ratio of 0.01.

9. The photocatalytic reactor of claim 7, further comprising the reactor catalyst surface having a photocatalyst coating.

10. The photocatalytic reactor of claim 7, further comprising the relative height ratio having a range of 0.01-0.1.

11. The photocatalytic reactor of claim 7, further comprising the relative width ratio being 0.02.

12. The photocatalytic reactor of claim 7, wherein the cross-sectional shape of each roughness element is an isosceles triangle.

* * * * *